(12) United States Patent
Fraley

(10) Patent No.: US 7,019,039 B1
(45) Date of Patent: Mar. 28, 2006

(54) HIGH EFFICIENCY PROCESS FOR PRODUCING METHANOL FROM A SYNTHESIS GAS

(75) Inventor: Lowell Fraley, Sugar Land, TX (US)

(73) Assignee: Starchem Technologies, Inc., Houston, TX (US)

( * ) Notice: Subject to any disclaimer, the term of this patent is extended or adjusted under 35 U.S.C. 154(b) by 0 days.

(21) Appl. No.: 11/181,267

(22) Filed: Jul. 14, 2005

(51) Int. Cl.
*C07C 27/00* (2006.01)

(52) U.S. Cl. .................. 518/700; 702/703; 702/705

(58) Field of Classification Search ........... 518/702, 518/703, 705, 700

See application file for complete search history.

(56) References Cited

U.S. PATENT DOCUMENTS 5,472,986 A * 12/1995 van Dijk ............... 518/705

* cited by examiner

*Primary Examiner*—J. Parsa
(74) *Attorney, Agent, or Firm*—Akin Gump Strauss Hauer & Feld LLP; Lester L. Hewitt

(57) ABSTRACT

This invention relates to a process for producing methanol from a synthesis gas produced by partial oxidation of natural gas with an oxidant stream having a high nitrogen content, such as an oxygen enriched air stream. This invention utilizes a high pressure non-permeate gas stream of low BTU content obtained from a partial expansion of a very high pressure tail gas of the process down to a high pressure together with a high pressure non-permeate gas stream of low oxygen content to achieve an energy efficient process by passing these non-permeate, high pressure streams in combination into contact with an oxidizing catalyst, so to significantly increase the temperature of these combine high pressure gas streams, for increased working energy recovery therefrom, as by their expansion through a hot gas expander.

8 Claims, 2 Drawing Sheets

HIGH EFFICIENCY PROCESS FOR PRODUCING METHANOL FROM A SYNTHESIS GAS

CROSS-REFERENCE TO RELATED APPLICATIONS

Not applicable.

STATEMENTS REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

1. Field of the Invention

This invention relates to a process for producing methanol from a synthesis gas produced by partial oxidation of natural gas with an oxidant stream having a high nitrogen content, such as air or an oxygen enriched air stream.

2. Description of the Related Art

Methanol, in addition to being a commodity chemical, is useful as a starting material in production of hydrocarbon compounds useful as liquid fuels or organic compounds. Methods for production of methanol are known. Chemical methods for production of methanol involve contacting a hydrogen ($H_2$), carbon monoxide (CO) and carbon dioxide ($CO_2$) containing synthesis gas composition at elevated pressure with a catalyst composition that promotes the reaction of $H_2$, CO and $CO_2$ to methanol.

Until recently, the chemical methods for catalytically preparing methanol from a synthesis gas have been too expensive to allow its use to make products that are competitive in cost with those produced by refining of crude oil.

Conventional methods of synthesis gas formation were capitally intensive; steam reforming of natural gas being expensive because of the energy input and equipment requirements and adiabatic reforming of natural gas being expensive because of its need for an oxidant stream of a low nitrogen content so as not to introduce inert species into the synthesis gas and also because of the need to perform a subsequent water-gas shift reaction and then a carbon dioxide ($CO_2$) removal process on the adiabatically formed synthesis gas to increase its $H_2$ content. The cost of either type of synthesis gas formation made the methanol produced therefrom too expensive to enable its use to produce products that are economically competitive to that refined from crude oil. This, until recently, has been the case.

U.S. Pat. Nos. 5,177,114 and 5,245,110 to Van Dijk et al. describe methods by which methanol can be produced from natural gas at a greatly reduced cost compared to methods previous thereto. Integral to these cost saving methods is the use of a gas turbine integrated into the process from which a portion of its compressed air (21% $O_2$, 79% $N_2$) is diverted to form the oxidant stream (either air or oxygen enriched air) for use in preparing a synthesis gas by adiabatic reforming—namely, partial oxidation—of methane, i.e., natural gas. A synthesis gas prepared by partial oxidation—i.e., adiabatic reforming—is considerably more economical to prepare than one produced by steam reforming of methane. Further reducing the cost of producing the synthesis gas is the fact that air or an oxygen enriched air is used as the oxidant stream for the partial oxidation reaction rather than oxygen ($O_2$) which requires production by a capitally expensive cryogenic $O_2$ separation unit. However, the use of air or an $O_2$ enriched air to produce the synthesis gas introduces into it a substantial quantity of nitrogen ($N_2$).

In the Van Dijk et al. method, this adiabatically formed synthesis gas of a high $N_2$ content is then converted to methanol by sequential passage through a series of methanol conversion reactors. Conversion through a series of reactors, rather than by recycle-passthrough of a single methanol conversion reactor, is required in the Van Dijk et al. methods because the high $N_2$ content of the synthesis gas would make the recycle gas requirement for conversion through a single reactor prohibitively expensive. As produced, the methanol is recovered between stages, or is left in the gas phase to be converted to other products such as gasoline or other hydrocarbons which is then recovered; either procedure leaving a final gas composition, or "tail gas," having a total heat of combustion BTU content and a BTU/scf heating value suitable for use as fuel for the gas turbine. All nitrogen introduced into the synthesis gas through that portion of compressed air diverted from the gas turbine compressor to form the oxidant stream passes as an inert component through all product conversion process steps so that the entirety of this nitrogen becomes a component of the tail gas remaining after the final step of product recovery. Hence, if all tail gas can be utilized as fuel for the gas turbine, such nitrogen which was initially diverted from passage from the compressor side to the energy production unit or expander side of the gas turbine is ultimately returned to that unit in the tail gas fuel.

Since maintenance of a proper mass balance between the compressor side and the expander side (which includes the turbine combustion unit) of a gas turbine is critical to its proper operation and life expectancy, the ultimate return of all of this initially diverted nitrogen to the expander side of the gas turbine is a significant concern in the practice of Van Dijk et al. methods. Unless this nitrogen is returned, the quantity of compressed air which may be taken from the compressor side of the gas turbine for use in forming a synthesis gas would be so limited as to be of no practical interest. Accordingly, it is of significant importance in the Van Dijk et al. methods that substantially the entirety of the tail gas resulting after the final product recovery step be capable of use as fuel for the gas turbine. To the extent that a portion of the tail gas cannot be used as gas turbine fuel because the tail gas as a whole has too great a total heat of combustion BTU content or an inadequate BTU/scf heating value, to that extent a quantity of the nitrogen initially diverted from the compressor side of the gas turbine is not returned to the expander side of the gas turbine and, accordingly, the quantity of compressed air that can be taken from the gas turbine for use in synthesis gas formulation is reduced. This then reduces the quantity of synthesis gas that can be produced which in turn increases the cost of production of the final product, especially as the capital cost obligations associated to the gas turbine contribute to final product cost.

Another aspect of the methanol production methods as described by the Van Dijk et al. U.S. Pat. Nos. 5,177,114 and 5,245,110 which is in need of improvement is that of the character of the synthesis gas. Production of methanol from a synthesis gas prepared by steam reforming has an advantage over that of a synthesis gas prepared by adiabatic reforming of methane. In a steam reformed synthesis gas—a typical composition of which is 15% CO, 8% $CO_2$, 74% $H_2$ and 3% $CH_4$, all as mole %—the quantity of $H_2$ in relationship to the content of CO and $CO_2$, expressed as a ratio of $(H_2)/(2CO+3CO_2)$ is at or above the stoichiometric value of 1.0 needed for conversion of all CO and $CO_2$ to methanol, typically with steam reforming this value being about 1.3–1.4. Such is not the case with respect to a synthesis gas prepared by adiabatic reformation wherein the value of this ratio is significantly less than 1.0, as on the order of about 0.8 to 0.90.

That the stoichiometric ratio of $H_2$ is less than 1.0 in an adiabatic reformation synthesis gas is in itself of no serious concern in the operation of the first or second reactors in a series of methanol conversion reactions. However, as the CO, $CO_2$ and $H_2$ content thereof is progressively reduced by conversion to methanol through a series of methanol conversion reactors the $H_2$ ratio of the remaining gas mixture may progressively depart even more greatly from the ideal stoichiometric $H_2$ value, and this offers reasons for concern in terms of selectivity to methanol and the life of methanol conversion catalyst exposed to the gas streams of progressively lesser stoichiometric $H_2$ value. Further, since the adiabatically formed syntheses gas is below the ideal stoichiometric $H_2$ value to start with, the quantity of methanol made over a given quantity of catalyst is less than could be achieved with a synthesis gas of ideal or greater stoichiometric $H_2$ ratio value. Also, the rate of conversion of an adiabatically produced synthesis gas is slower than when using a steam reformed synthesis gas of similar partial pressure of the reacting species.

U.S. Pat. No. 5,472,986 to Van Dijk describes a solution to the above stated stoichiometric $H_2$ ratio problem. Van Dijk U.S. Pat. No. 5,472,986 describes a method for processing natural gas into methanol by first converting natural gas by adiabatic reforming with use of an oxidant gas stream secured from a portion of compressed air taken from the compressor side of a gas turbine into a synthesis gas and combining that synthesis gas with a gas stream having a high content of hydrogen which is secured by diffusion of the process tail gas through a semipermeable membrane selective for the permeation of $H_2$ in comparison to $N_2$. Provided that the conditions of operation of the natural gas to methanol conversion process are properly limited, the non-permeate portion of the tail gas has a total heat of combustion BTU content and a BTU/scf heating value which allows its use in its entirety as fuel for the gas turbine and is returned to the energy production unit of the expander side thereof as fuel. The hydrogen rich permeate is compressed and combined with the synthesis gas in a quantity sufficient to provide a combined synthesis-recycle gas stream having a $H_2$ ratio expressed as $(H_2)/(2CO+3CO_2)$ which is about or greater than 1.0.

However, even though an improvement, the process of Dijk U.S. Pat. No. 5,472,986 is still restricted to the limits that proper gas turbine operation imposes on the freedoms of the chemical operations within the process. There is still a desire in the art for an economical process for the production of methanol from natural gas (a gas to liquid conversion, or GTL operation) that is not subject to the limitation which a gas turbine would impose upon the GTL process.

BRIEF SUMMARY OF THE INVENTION

This invention comprises an energy efficient process for the production of methanol from natural gas which is not subject to the limitations upon the freedom of chemical operations that a gas turbine integrated within such process, as is the case with the process of Van Dijk U.S. Pat. No. 5,472,986, would impose. In the process of this invention air is compressed by a conventional air compressor to an elevated pressure (i.e., about 185 psi) suitable to diffuse such compressed air through a semipermeable membrane, preferential for permeation of $O_2$ in preference to $N_2$, into a low pressure permeate stream enriched in oxygen compared to air (i.e., preferable $\geq 40$ mole % $O_2$) and leaving a high pressure non-permeate stream which is poor in oxygen content compared to air (i.e., $\leq 10$ mole % $O_2$). This $O_2$ enriched air is then compressed and used for adiabatic reforming of a pressurized natural gas (preferably, desulfurized). A hydrogen rich gas stream (i.e., about 14–19 mole % $H_2$) is obtained as a permeate gas stream by diffusion from the process tail gas and is recompressed and recycled into admixture with the synthesis gas. This combined synthesis-hydrogen recycle gas stream is then compressed (i.e., to about 700 psi), heated (i.e., to about 415° F.) then fed to the first of a plurality of methanol conversion reactors wherein the gas contacts a methanol conversion catalyst to react a portion of the $H_2$, CO and $CO_2$ content of the gas to methanol. Following the reaction the effluent gas from the methanol reactor is cooled and passed to a separator wherein a liquid phase of methanol and water is separated from the remainder of the synthesis-hydrogen recycle gas stream. The remainder of the synthesis-hydrogen recycle gas stream is then reheated and passed to the next in the series of the plurality of methanol conversion reactors wherein the process of conversion to methanol, methanol-water removal, and the remainder of the synthesis-hydrogen recycle gas stream reheat for feed to the next of the series of methanol reactors, as described above for the first reactor, is repeated. This stepwise processing is repeated until the synthesis-hydrogen recycle gas stream has passed through all of the methanol reactors of the series. Following methanol and water removal from the effluent gas of the last methanol reactor, the remainder of the gas stream, that is, the process "tail gas" is passed to a membrane diffusion unit which is preferential for the diffusion of $H_2$ compared to $N_2$ to form a low pressure hydrogen rich permeate gas stream which is recompressed and then fed into combination with the synthesis gas prior to its first contact with a methanol catalyst.

The very high pressure non-permeate portion of the tail gas stream which is of a low BTU content is partially expanded through a hot gas expander for recovery of working energy and the so expanded tail gas is then combined with the high pressure non-permeate stream which is poor in oxygen content compared to air that was left from diffusion of compressed air to produce the oxidant stream and these gas streams are sent to an oxidizer for oxidization of the low oxygen and low BTU content of this combined gas stream over an oxidizing catalyst so to utilize the low BTU and low oxygen content of the combine gas streams to increase the temperature of these combined high pressure gas streams for increased working energy recovery by their expansion through a hot gas expander.

BRIEF DESCRIPTION OF THE SEVERAL VIEWS OF THE DRAWINGS

FIG. 1 illustrates the synthesis gas production unit and FIG. 2 illustrates the methanol production and energy recovery units.

DETAILED DESCRIPTION OF THE INVENTION

Figure 1:
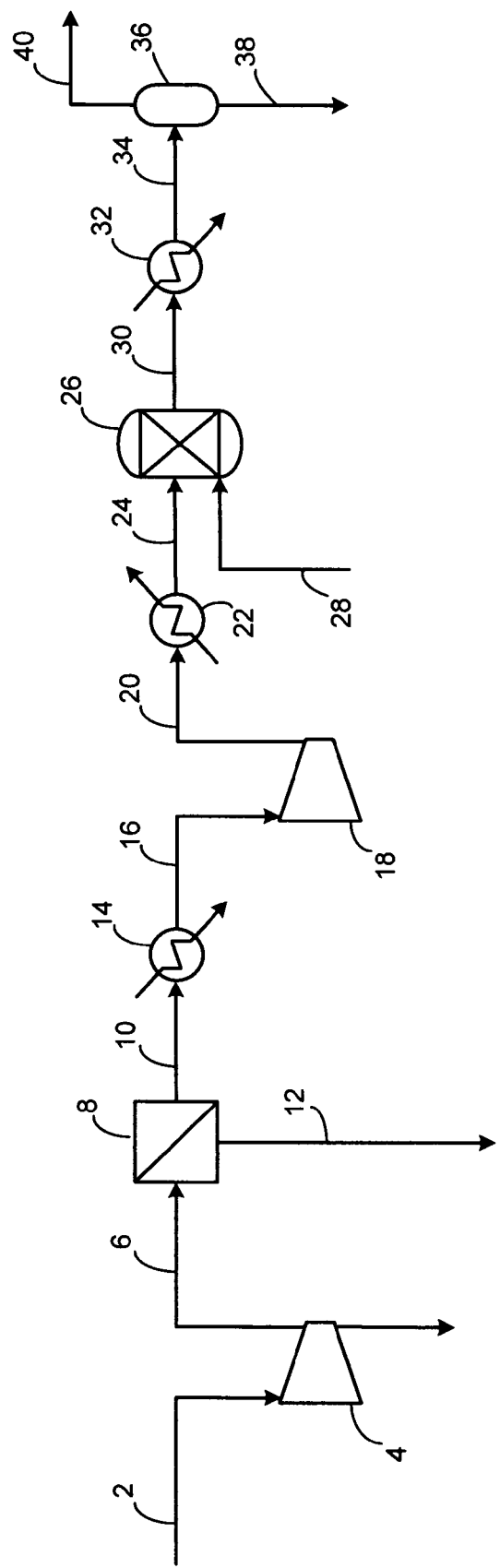
FIGS. 1–2, together illustrate an embodiment of the present invention wherein a hydrogen rich gas stream is obtained as a permeate gas stream by diffusion from the process tail gas and is recompressed and recycled into admixture with a synthesis gas formed by partial oxidation of natural gas with an oxidant stream obtained as a permeate gas stream by diffusion from compressed air taken from a conventional air compressor, rather than from a gas turbine, with the high pressure non-permeate portion from diffusion of the tail gas and the high pressure non-permeate portion from diffusion of the compressed air returned to an oxidizer for oxidization over an oxidizing catalyst so to increase the temperature of these high pressure gas streams for increased energy recovery by their expansion through a hot gas expander.

This invention comprises an energy efficient process for the production of methanol from natural gas, which process is not subject to the limitations upon the freedom of chemical operations that an integrated gas turbine, as is the case with the process of Van Dijk U.S. Pat. No. 5,472,986, would impose. This invention utilizes a high pressure non-permeate gas stream of low BTU content obtained from a partial expansion of a very high pressure (i.e., about 786 psi) tail gas of the process down to a high pressure (i.e., about 176 psi) together with a high pressure non-permeate gas stream of low oxygen content (i.e., about 176 psi) to achieve this energy efficient process by passing these non-permeate, high pressure streams (i.e., about 176 psi) in combination into contact with an oxidizing catalyst, so to significantly increase the temperature of these combine high pressure gas streams, for increased working energy recovery therefrom, as by their expansion through a hot gas expander.

The invention comprises a method for converting a sub-stoichiometric synthesis gas—i.e., one in which the $H_2$ content is stoichiometrically insufficient for conversion of its CO and $CO_2$ content—into methanol with all advantages inherent in the conversion of a stoichiometrically correct synthesis gas. The synthesis gas may be prepared by adiabatic reforming with an oxidant gas stream comprising $O_2$ enriched air produced by use of conventional compressors for compression of air which is then diffused through a membrane unit which is preferential for permeation of $O_2$ in preference to $N_2$ to produce a low pressure permeate stream which is enriched in oxygen compared to air, which is used as the oxidant gas stream, and leaving a high pressure (i.e., about 176 psi) non-permeate stream which is poor in oxygen content compared to air. The very high pressure (i.e., about 831 psi) tail gas remaining after the final step of product recovery is diffused through a membrane which is preferential for permeation of $H_2$ over $N_2$ and the $H_2$ rich permeate is compressed and combined with a synthesis gas prepared by adiabatic reforming of natural gas in a quantity sufficient to provide a combined synthesis-recycle gas stream having a $H_2$ content that is about or above the stoichiometric amount required for conversion of its CO and $CO_2$ content to methanol. The very high pressure non-permeate portion of the tail gas is partially expanded through a hot gas expander for recovery of working energy until the so expanded tail gas is about equal in pressure to that of the high pressure non-permeate stream which is poor in oxygen content compared to air that was left from compressed air diffusion to produce the oxidant stream, and these gas streams are sent in combination to an oxidizer for oxidization over an oxidizing catalyst so to significantly increase the temperature of these high pressure gas streams for increased working energy recovery, i.e., such as by their subsequent expansion through a hot gas expander.

With the process or this invention, natural gas may be converted to methanol, or other products derived from methanol, by the treatment of an adiabatically formed synthesis gas through a series of conversion reactors, this with all advantages as if the synthesis gas was ideally balanced with respect to the stoichiometric quantity of $H_2$ required for conversion of its CO and $CO_2$ content to methanol. The synthesis gas is prepared with an oxidant gas stream secured from compressed air taken from a conventional air compressor. The tail gas remaining after the final stage of product recovery is diffused through a membrane preferential for the permeation of $H_2$ relative to $N_2$ and the $H_2$ rich permeate is compressed and recycled into combination with the synthesis gas to enrich its $H_2$ content to about or in excess of the stoichiometric quantity of that $H_2$ required to convert the CO and $CO_2$ content of the combined synthesis-recycle gas stream to methanol and the non-permeate tail gas stream is employed as the fuel for an oxidation reaction with the oxygen of the high pressure non-permeate oxygen poor stream remaining after diffusion to prepare the $O_2$ enriched air use in adiabatic formation of the synthesis gas.

Figure 2:
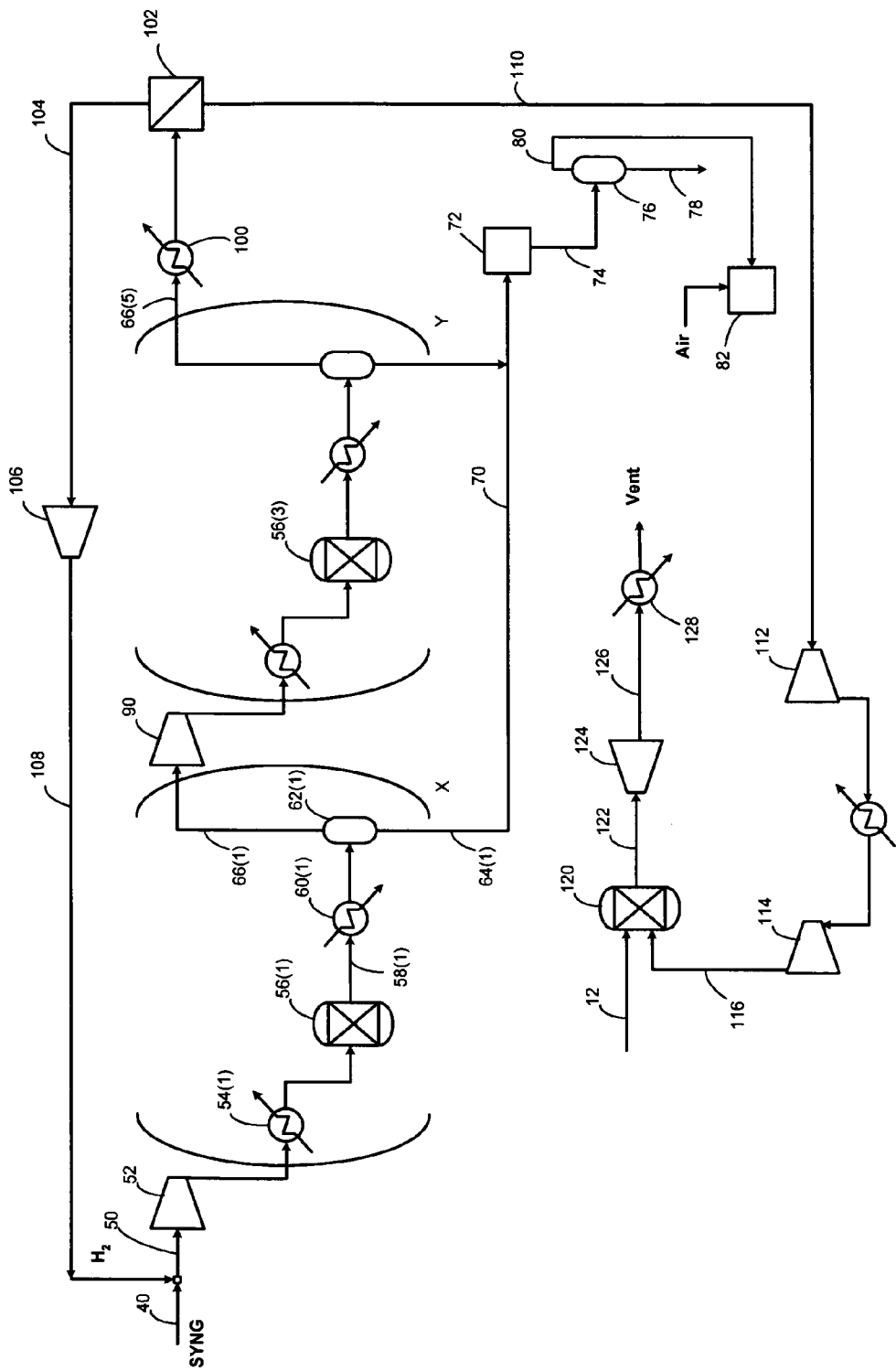

FIGS. 1–2, together illustrate an embodiment of the present invention which utilizes a series of methanol conversion reactors with interstage recovery of methanol. Air 2 is compressed in an air compressor 4 and compressed air stream 6 is fed to an oxygen enrichment membrane diffusion unit 8 which preferentially diffuses oxygen in preference to nitrogen. A low pressure oxygen rich permeate gas stream 10 and a high pressure oxygen poor, or nitrogen rich, non-permeate gas stream 12 are formed. The oxygen-rich permeate gas stream 10 is cooled in heat exchanger 14, then passed by line 16 to compressor 18 where it is compressed, then the compressed air is passed by line 20 to heat exchanger 22 where it is heated and then it is passed by line 24 into an adiabatic reformer reactor 26 into which pressurized natural gas 28 (preferably, desulfurized) is also passed. There the natural gas is partially oxidized—i.e., adiabatically reformed—to produce a synthesis gas containing $H_2$, CO, $CO_2$, and other components wherein the ratio of $(H_2)/(2CO+3CO_2)$ is about or less than 0.85. Preferably, the synthesis gas 30 is cooled in heat exchanger 32 and passed by line 34 to separator 36 where water is condensed and removed from this synthesis gas by line 38 and thereafter synthesis gas 40 is combined with a hydrogen rich recycle gas stream supplied by line 108 (as seen in FIG. 2). The hydrogen rich gas stream is supplied in an amount that upon its combination with the synthesis gas forms a combined synthesis-hydrogen recycle gas stream 50 wherein the ratio of $(H_2)/(2CO+3CO_2)$ is at least about 0.95, and preferably 1.0 or greater.

As shown in FIG. 2, this combined synthesis-hydrogen recycle gas stream 50 is then compressed by compressor 52, then heated in heat exchanger 54(1), then fed to the first of a plurality (X+Y) of methanol conversion reactors 56(1) wherein the gas contacts a methanol conversion catalyst to react a portion of the $H_2$, CO and $CO_2$ content of the gas to methanol. Following the reaction the effluent gas 58(1) from methanol reactor 56(1) is cooled by a chill water heat exchanger 60(1) and passed to separator 62(1) wherein a liquid phase 64(1) of methanol and water is separated from the remainder of the synthesis-hydrogen recycle gas stream 66(1). The remainder of the synthesis-hydrogen recycle gas stream is then passed to the next in series of the plurality of methanol conversion reactors wherein the process of synthesis-hydrogen recycle gas stream reheating, conversion to methanol and methanol-water removal, as described above for the first reactor, is repeated. Accordingly, each reactor of the series will have heat-up heat exchanger like 54(1), a cool down heat exchanger like 60(1), a separator like 62(1) with a product take-off line like 64(1) and synthesis-hydrogen recycle gas stream take-off line 66(1) all as illustrated in reactor 56(1). This stepwise processing is repeated until the synthesis-hydrogen recycle gas stream has passed through all of the x+y number of methanol reactors of the series (here a five reactor series is illustrated, but the number may vary as desired). All product take-off lines 64(1–5) are fed by line 70 to mixer 72 which then by line 74 feeds a methanol stabilizer column 76. Methanol 78 is taken at the bottom from column 76 and the overhead gases 80 are sent to burner 82 and eventually vented. Optionally, but preferably, the overhead synthesis-hydrogen recycle gas stream leaving separator 62(2) of the second reactor 56(2) is recompressed in compressor 90 and thereafter fed to the third reactor 56(3). Following methanol and water removal from the effluent gas of the last methanol reactor 56(5), the remainder of the gas stream 66(5), that is, the process "tail gas" is heated in heat exchanger 100 then passed to a hydrogen enrichment membrane diffusion unit 102 which is preferential for the diffusion of $H_2$ compared to $N_2$ to form a hydrogen rich permeate gas stream 104 which is recompressed by compressor 106 and fed by line 108 into combination with synthesis gas 40. The non-permeate portion of the tail gas stream 110 is fed to a hot gas expander 112 and 114 for recovery of energy and the expanded tail gas 116 is then fed to a catalytic oxidation reactor 120. The oxygen poor non-permeate 12 from the oxygen enrichment membrane diffusion unit 8 is also fed to a catalytic oxidation reactor 120. In the oxidation reactor all oxidizable components of the two feed streams, 12 and 116, are catalytically oxidized to increase the temperature of effluent gas stream 122. that exits this reactor. This effluent gas stream 122. is then fed to a hot gas expander 124 for recovery of energy after which the so expanded gas 126 is cooled in heat exchanger 128 and the gas so cooled is vented.

The fuel gas to the combustor contains CO which requires a catalyst to insure near complete combustion to $CO_2$. Many catalysts for this purpose are known in the art. Among other applications, these were developed for use in gas turbines and the exhaust of internal combustion engines. Normally, the catalyst material is deposited on a carrier. Typically, catalyst material can be palladium, platinum, rhodium and ruthenium. The carrier can be a ceramic selected from the group consisting of alumina, bauxite, sillimanite, petalite, cordierite, mullite, zircon, zircon mullite, spodumene, titania and alumina-titanate. Promoters are sometimes included. These can be an element selected from the group formed by lanthanum, cerium, praseodymium, neodymium, barium, strontium, calcium and oxides thereof. Or they can be an element selected from the group formed by magnesium, silicon and oxides thereof. Additionally they can be an element selected from the group formed by nickel, zirconium, cobalt, iron and manganese and oxides thereof.

Many types of membrane materials are known in the art which are highly preferential for diffusion of hydrogen compared to nitrogen. Such membrane materials include those composed of silicon rubber, butyl rubber, polycarbonate, poly(phenylene oxide), nylon 6,6, polystyrenes, polysulfones, polyamides, polyimides, polyethers, polyarylene oxides, polyurethanes, polyesters, and the like. In the process of this invention the membrane material selected is preferably also highly preferential for diffusion of hydrogen compared to carbon dioxide, although this preference is by no means critical to the practice of this invention. Accordingly, membrane materials like those discussed in U.S. Pat. No. 4,181,675 which also provided for significant codiffusion of $CO_2$ may also be readily utilized in this invention. The membrane units may be of any conventional construction, and a hollow fiber type construction is preferred.

As appreciated by those skilled in the art, the syn gas entering the reaction system has carbon in excess of the hydrogen, i.e., the gas is less than stoichiometric for conversion to methanol. The excess carbon is rejected from the system so that all reactors receive gas that is greater than stoichiometric. The rejection occurs at the hydrogen membrane. 95% of the hydrogen entering the reactor system is blocked from leaving the system by the membrane. The retained hydrogen can only leave the system as reaction products, methanol and water. The number of reactors is selected so that most of the CO is reacted before the process gas enters the membrane. Some $CO_2$ diffuses with the retained hydrogen and stays to react in the system but most flows out of the system along with the CO. About 8% of the CO and 50% of the CO2 entering the system as syn gas is rejected from the reactor system and becomes fuel for the catalytic oxidizer. This carbon rejection maintains the reactor system higher than stoichiometric.

We claim:

1. A process for converting natural gas to methanol comprising the steps of:

partially oxidizing natural gas with an oxidant stream to form a synthesis gas containing $H_2$, CO and $CO_2$ in a ratio of $(H_2)/(2CO+3CO_2)$ less than 1.0, said oxidant stream secured by diffusion of compressed air through a semipermeable membrane preferential for permeation of $O_2$ in preference to $N_2$ into a low pressure permeate stream enriched in oxygen compared to air and leaving a high pressure non-permeate stream which is poor in oxygen content compared to air;

combining the synthesis gas with a hydrogen rich recycle gas stream, said hydrogen rich recycle gas stream being used in an amount that provides a combined synthesis-recycle gas stream containing $H_2$, CO and $CO_2$ in a ratio of $(H_2)/(2CO+3CO_2)$ which is greater than that of the synthesis gas;

passing said combined synthesis-recycle gas stream into a plurality of contacts with a methanol conversion catalyst with recovery of methanol from said gas stream between contacts with the methanol conversion catalyst to form after the last methanol recovery step a tail gas stream which is subjected to diffusion through a semipermeable membrane preferential for permeation of $H_2$ in preference to $N_2$ to produce as a low pressure permeate stream the hydrogen rich gas stream for recycle and leaving a high pressure non-permeate stream which is of a reduced hydrogen content;

passing said high pressure non-permeate stream which is poor in oxygen content into admixture with said high pressure non-permeate stream which is of a reduced hydrogen content over an oxidizing catalyst to form an oxidized gas stream, and recovering energy from said oxidized gas stream.

2. The process of claim 1, wherein, energy is recovered from said oxidized gas stream by expanding said gas stream.

3. The process of claim 1, wherein said synthesis gas has a ratio of $(H_2)/(2CO+3CO_2)$ of 0.85 or less.

4. The process of claim 3, wherein the combined synthesis-recycle gas stream has a ratio of $(H_2)/(2CO+3CO_2)$ of 0.95 or greater.

5. The process of claim 4, wherein the combined synthesis-recycle gas stream is passed into at least three contacts with a methanol conversion catalyst.

6. The process of claim 1, wherein the oxidant stream contains at least about 40 mole % oxygen.

7. The process of claim 1, wherein the high pressure non-permeate stream which is poor in oxygen content contains less than about 10 mole % oxygen.

8. The process of claim 1, wherein energy is first recovered from said the high pressure non-permeate stream which is of a reduced hydrogen content by expanding said gas stream until its pressure is equal to that of said non-permeate stream which is poor in oxygen content compared to air and thereafter passing said high pressure non-permeate stream which is poor in oxygen content into admixture with said non-permeate stream which is of a reduced hydrogen content over an oxidizing catalyst to form an oxidized gas stream.

* * * * *